US010016128B2

(12) United States Patent
Evans

(10) Patent No.: US 10,016,128 B2
(45) Date of Patent: Jul. 10, 2018

(54) METHOD AND APPARATUS FOR VISION ACUITY TESTING

(71) Applicant: Ceatus Media Group LLC, San Ramon, CA (US)

(72) Inventor: David Evans, San Diego, CA (US)

(73) Assignee: David Evans, San Diego, CA (US)

(*) Notice: Subject to any disclaimer, the term of this patent is extended or adjusted under 35 U.S.C. 154(b) by 34 days.

(21) Appl. No.: 15/277,849

(22) Filed: Sep. 27, 2016

(65) Prior Publication Data

US 2018/0084990 A1    Mar. 29, 2018

(51) Int. Cl.
   *A61B 3/02*      (2006.01)
   *A61B 3/032*     (2006.01)
   *A61B 3/00*      (2006.01)

(52) U.S. Cl.
   CPC ............ *A61B 3/032* (2013.01); *A61B 3/0008* (2013.01); *A61B 3/0025* (2013.01); *A61B 3/0041* (2013.01)

(58) Field of Classification Search
   CPC .......... A61B 1/06; A61B 3/0033; A61B 3/032
   USPC ................. 351/246, 237, 211, 243, 222, 205
   See application file for complete search history.

(56) References Cited

U.S. PATENT DOCUMENTS

| 5,325,136 A | 6/1994 | Salibello |
| 8,414,126 B2* | 4/2013 | Giraudet .................. A61B 5/16 351/222 |
| 2008/0018855 A1 | 1/2008 | Larichev |
| 2010/0165294 A1 | 4/2010 | Barbur |
| 2011/0228228 A1 | 9/2011 | Butler |
| 2015/0313458 A1 | 11/2015 | Butler |
| 2016/0228001 A1 | 8/2016 | Choate |

OTHER PUBLICATIONS

Office Action dated Nov. 30, 2017, U.S. Appl. No. 15/445,586.
International Search Report dated Apr. 19, 2018, PCT/US2017/053473.

* cited by examiner

*Primary Examiner* — Hung Dang
(74) *Attorney, Agent, or Firm* — Calvin B. Ward

(57) ABSTRACT

A vision testing system and a method of operating a data processing system for displaying an eye test pattern on a computer display to a patient during an eye examination are disclosed. The method includes causing the data processing system to display the eye test pattern in a chart region of a computer display controlled by the data processing system and characterized by a luminance in regions not displaying the eye test pattern. An intensity of light leaving the computer display is measured in a sensor region outside the chart region using a display luminance sensor. The luminance of the computer display is adjusted to provide a light level within a predetermined range of light levels based on the measured intensity of light. The data processing system can receive the measured intensity and adjust the display luminescence.

17 Claims, 5 Drawing Sheets

METHOD AND APPARATUS FOR VISION ACUITY TESTING

BACKGROUND

Vision performance standards in the United States, and around the world, rely on visual acuity testing that relies on presenting a range of black letters on a white background to patients. Studies show that the test results can vary greatly based on the type of vision test used and the conditions in which the test is administered.

To ensure standardization, a number of recommended parameters for visual acuity testing have been established, including letter height, letter width, letter spacing, letter type, scoring procedures, testing distance and testing luminance. Clinicians, in general, have adopted these testing parameters. But, standardization of test lighting has not been adopted and this is an area of extreme need. Data shows that results of the acuity test vary greatly dependent on the testing light levels. It is well established that higher light levels produce significantly better vision results than lower light levels and that older patients are more affected by testing light levels than younger patients.

While the need for standardization has been recognized for some time, luminance standards have not heretofore been adopted by practicing eye doctors primarily because most eye doctors used the same type of vision testing equipment, which inherently created less variance due to the similarities of the devices. In addition, the required accuracy of vision testing was not such that differences in luminance levels between examination lanes or between eye clinics would create a problem for documenting the visual performance.

However, these two factors have now changed. Many eye doctors are no longer using the same types of devices for vision testing, greatly increasing the variability of luminance levels used between doctors. The projection systems that were common in the past have been replaced by computer displays that have widely varying luminance, and hence, the variability between test systems has increased substantially.

In addition, many new vision correction surgical techniques are being developed which are driving a need to improve the accuracy of vision test results in order to document the benefits of surgery and so that the outcomes of different types of procedures can be accurately compared. Further, United States government healthcare reimbursement agencies are moving to a system in which eye doctors will be reimbursed for services based on the quality of the visual outcomes related to treatment. This change in reimbursement strategies will by necessity require more accuracy in the measurement of visual acuity, since visual acuity is the primary outcome measure for the vast majority of eye treatments.

SUMMARY

The present invention includes a vision testing system and a method of operating a data processing system for displaying an eye test pattern on a computer display to a patient during an eye examination. The method includes causing the data processing system to display the eye test pattern in a chart region of a computer display controlled by the data processing system and characterized by a luminance in regions not displaying the eye test pattern. An intensity of light leaving the computer display is measured in a sensor region outside the chart region using a display luminance sensor. The luminance of the computer display is adjusted to provide a light level within a predetermined range of light levels based on the measured intensity of light.

In one aspect of the invention, adjusting the luminance includes receiving the measured intensity by the data processing system and automatically adjusting the computer display in response to the measured intensity.

In another aspect, the light intensity is measured by a sensor that views a portion of the computer display and wherein the sensor communicates directly with a user of the data processing system with instructions on changing the luminance of the computer display.

In another aspect of the invention, the method includes providing an ambient light sensor proximal to the patient's eyes that measures a light intensity in a room containing the patient and causing the data processing system to alter the ambient light intensity in the room such that the light intensity in the room is within predetermined limits.

In another aspect of the invention, the ambient light sensor is positioned such that light from the computer display is not directly received by the ambient light sensor.

In another aspect of the invention, the method includes measuring the luminance of the display in the chart region, and measuring the luminance in the sensor region, the data processing system calibrating the measured luminance in the sensor region to the measured luminance in the chart region.

In another aspect of the invention, the display luminance sensor is used to measure the luminance in both the chart region and the sensor region.

In another aspect of the invention, the method includes providing a glare light source proximately located to the chart region, the glare light source is characterized by a glare luminescence, measuring the glare luminescence with the light luminance sensor, and causing the data processing system to adjust the glare light source intensity such that the measured glare luminescence is within a predetermined range.

A vision testing system according to the present invention includes a data processing system, a luminance sensor, and a display intensity adjustment system. The data processing system includes a computer display, characterized by a display luminance, on which the data processing system displays an eye test pattern in a chart region of the computer display. The luminance sensor is positioned to measure a light intensity in a sensor region of the computer display, the sensor region being outside of the chart region. The display intensity adjustment system receives an output from the luminance sensor and causes the computer display to change the display luminance such that the output from the luminance sensor is within predetermined limits.

In one aspect of the invention, the display intensity adjustment system is separate from the data processing system.

In another aspect of the invention, the display intensity adjustment system includes a program running on the data processing system which automatically adjusts the display luminance in response to the measured light intensity in the sensor region.

In another aspect of the invention, the display intensity adjustment system includes an interface that instructs a user of the system to manually change the display luminance.

In another aspect of the invention, the luminance sensor reversibly attaches to the computer display.

In another aspect of the invention, the luminance sensor is powered by light received from the computer display.

In another aspect of the invention, the system includes an ambient light sensor positioned proximate to a patient's head to measure ambient light at a location of a patient's eyes and to communicate the measured ambient light to the data processing system.

In another aspect of the invention, the data processing system causes the ambient light to be changed such that the measured ambient light is within predetermined limits.

In another aspect of the invention, the system includes a glare source that includes a light source in close proximity to the chart region, the glare source emitting light characterized by a glare luminescence, wherein the illumination sensor measures the glare luminescence and the data processing system adjusts the glare luminescence such that the glare luminescence is within a predetermined range.

DETAILED DESCRIPTION

The present invention is based on the observation that computer displays not only deviate from display to display in luminance, but are also subject to changes when the display is used for other tasks, as the operator can adjust the display brightness to suit his or her needs. Hence, a mechanism that adjusts the luminance to the desired range at the start of the eye examination is required to guarantee that the examination is performed under standardized conditions.

Figure 1:
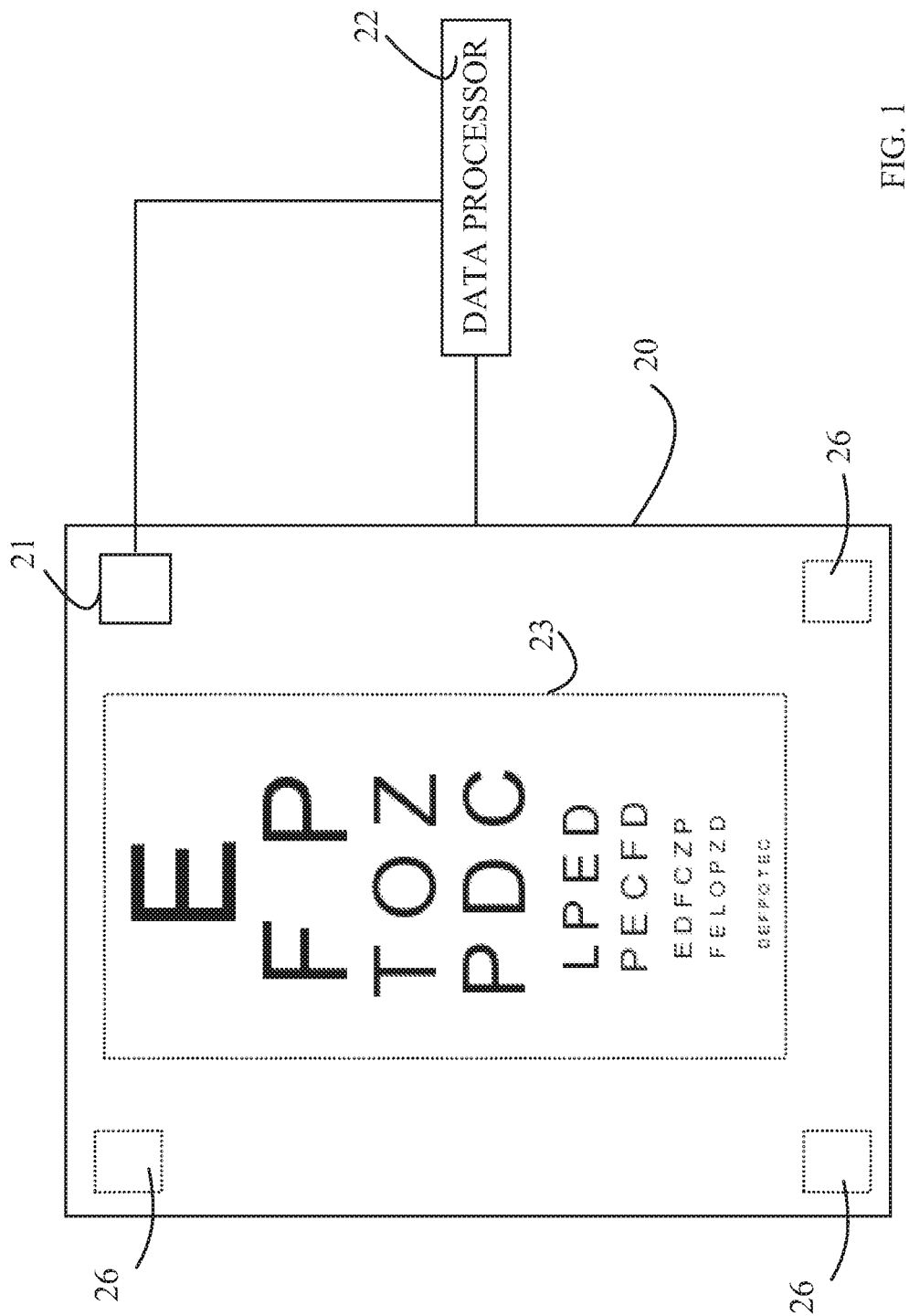
FIG. 1 illustrates a display according to one aspect of the present invention.

Refer now to FIG. 1, which illustrates a display according to one aspect of the present invention. Display 20 is connected to a controller, which is typically a conventional data processing system 22. The controller causes display 20 to display a conventional eye chart in a chart display area 23. A removable sensor 21 is positioned on display 20 in an area that is not used for the eye chart. Sensor 21 measures the average intensity of the light leaving display 20 and communicates that measurement to data processing system 22. Data processing system 22 then adjusts the intensity of display 20 such that the measured light intensity is within a predetermined intensity range. In one embodiment, sensor 21 is connected to data processing system 22 by a conventional USB port. In this embodiment sensor 21 is powered by data processing system 22. In another embodiment, sensor 21 is self-powered and communicates with data processing system 22 via a wireless communication link. In embodiments that utilize WiFi communication links, sensor 21 can include a server that can be accessed via a conventional browser to view the measured light levels and lead the user through any calibration procedure.

In one aspect of the invention, sensor 21 can be moved to different locations on display 20 to measure the intensity of light leaving the display at various locations. Computer displays are known to exhibit intensity variations across the display screens. These variations can be monitor specific. Hence, using the average luminescence over a limited area of the screen, particularly at one corner, as a proxy for the luminescence in the chart display area can be misleading. Hence, it is advantageous to measure the intensity at various locations in the chart display area and determine the relationship between the average luminescence in the chart display area and the luminescence at the sensor location. Accordingly, in one aspect of the present invention, data processing system 22 or sensor 21 includes software for mapping the luminescence of display 20 in the chart display region and at the location at which sensor 21 normally resides.

Embodiments in which multiple sensors measure the luminescent profile of the display can also be constructed. For example, optional sensors 26 shown in FIG. 1 can be placed at other locations on the display to measure the variations in screen intensity across the screen. These sensors also communicate with data processing system 22; however, to simplify the drawing, the connections between sensors 26 and data processing system 22 have been omitted.

Figure 2:
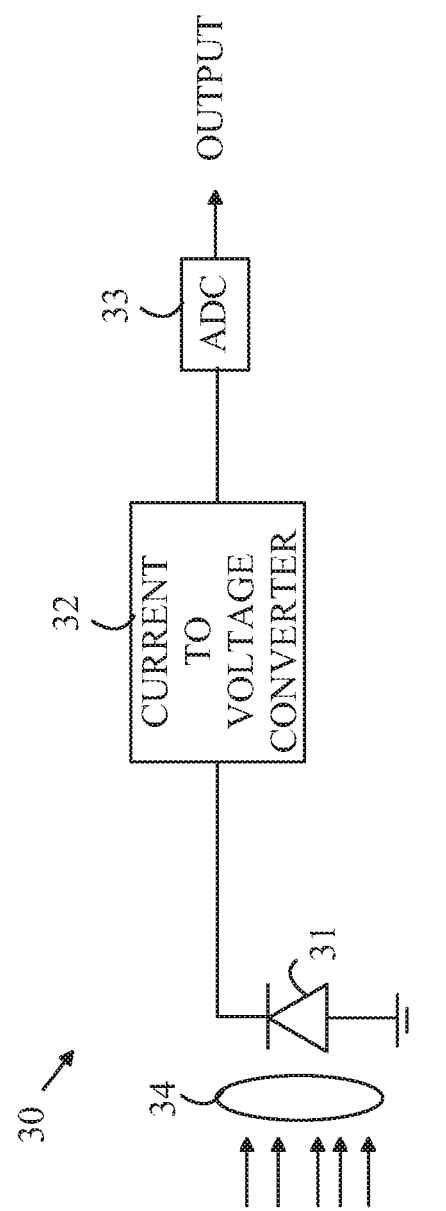
FIG. 2 illustrates one embodiment of an luminescence sensor that can be utilized in the present invention.

Refer now to FIG. 2, which illustrates one embodiment of a luminescence sensor that can be utilized in the present invention. Sensor 30 includes a photodiode 31 that receives light from a region on display 20. An optional lens 34 collects light from the display over an area that is greater than the area of photodiode 31. The area of light that is routed to photodiode 31 must be sufficient to average any pixel to pixel variations in display 20. The current from photodiode 31 is proportional to the luminescence of the monitored area. The current is converted to a voltage by current-to-voltage converter 32. The output of current-to-voltage converter 32 is digitized by analog-to-digital converter (ADC) 33 and forms the output that is used by the processing programs or other circuitry to adjust the display luminescence or provide feedback to the user on how to adjust the display luminescence.

Figure 3:
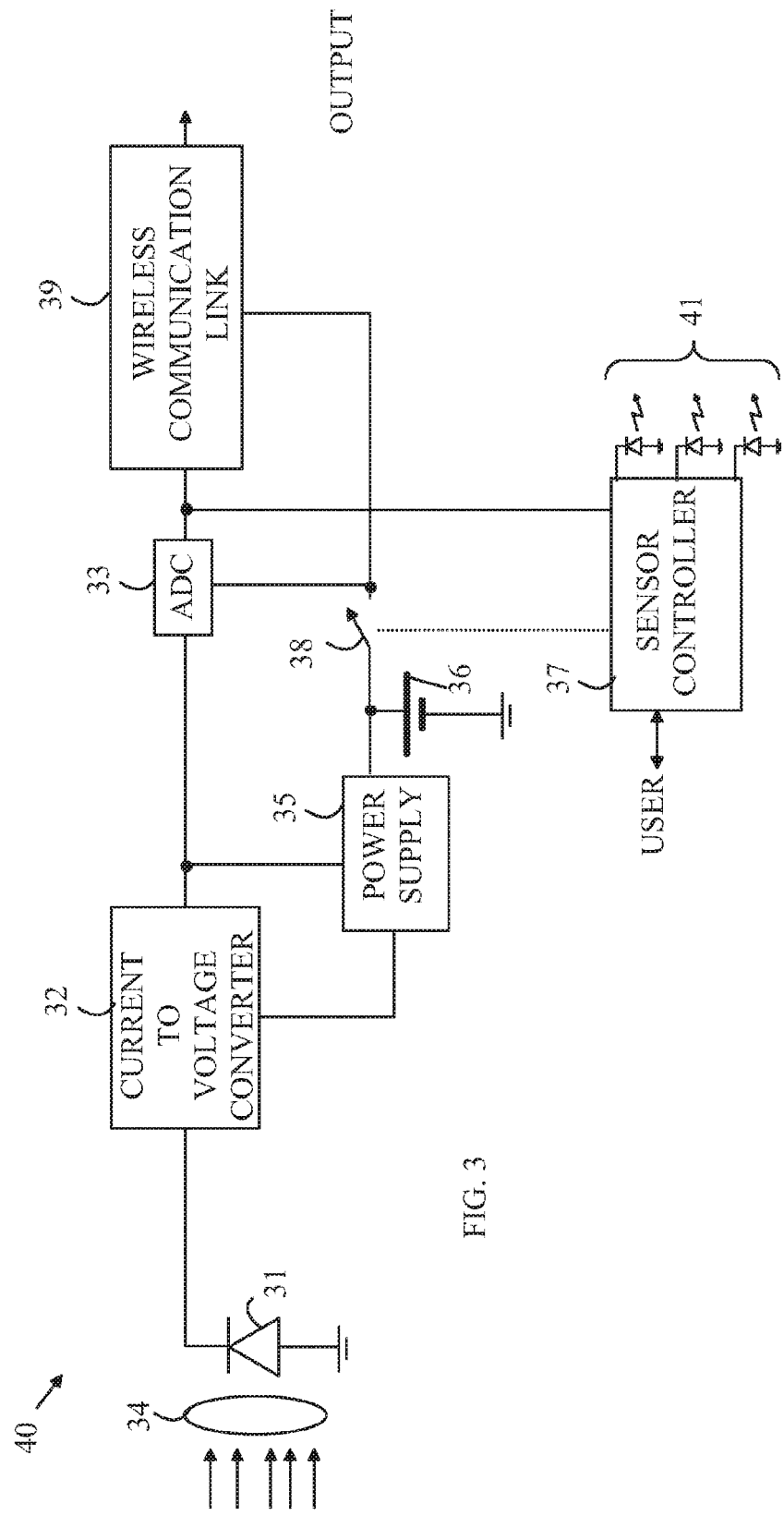
FIG. 3 illustrates one embodiment of a self-powered sensor according to the present invention.

In embodiments of the present invention that are not connected to the data processing system by a wired connection that also supplies power to the sensor, the sensor must be self-powered. It is advantageous to avoid schemes in which the sensor is battery powered by a battery that must be replaced periodically. In one aspect of the present invention, the photodiode is also used to power the sensor in embodiments in which the sensor is not connected to the data processing system by a wired link. Refer now to FIG. 3, which illustrates one embodiment of a self-powered sensor according to the present invention. Sensor 40 taps the output of current-to-voltage converter 32 to run a power supply 35 which optionally charges a rechargeable battery 36. The output of power supply 35 is used to power the electronics in sensor 40. To simplify the drawing, the connections between power supply 35 and the other components of sensor 40 have been omitted from the drawing. The amount of power that is available from photodiode 31 depends on the area of the display screen viewed by photodiode 31 and the intensity of light leaving that area. If the instantaneous power available from photodiode 31 is insufficient to power sensor 40, rechargeable battery 36 provides a mechanism for accumulating and storing the power output from photodiode 31 over time. In this regard, it should be noted that the amount of time that display 20 is dedicated to performing eye examinations is relatively small in most clinical settings. Hence, even a small current from photodiode 31 can provide the necessary power to power sensor 40 if the display is left on in the region viewed by photodiode 31.

To conserve power when sensor 40 is not operating to adjust the luminescence from display 20, switch 38 is opened to remove power from the ADC 33 and wireless communication link 39. Since wireless communication link 39 requires significant power when it is on, powering down these components saves power while allowing rechargeable battery 36 to be charged from the output of photodiode 31. When sensor 40 is being utilized to adjust the luminescence of display 20, the user signals sensor controller 37 to close switch 38.

In the above-described embodiments, sensor 40 is configured to operate in communication with the data processing system that controls the display and provides the chart for viewing by the patient such that the data processing system adjusts the luminescence of display 20 directly. However, embodiments of the present invention in which sensor 40 provides a standalone configuration can also be constructed. In such embodiments sensor controller 37 communicates with the user directly to adjust the luminescence of display 20. In one embodiment, sensor controller 37 includes a plurality of LEDs 41 that are viewable by the user who adjusts the luminescence of display 20 manually until sensor controller 37 indicates that the luminescence is in the desired range. To aid in the adjustment, one of the LEDs can be used to signal that the luminescence is too high, one to signal that the luminescence is too low, and one to signal that the luminescence is within the desired range. In such an embodiment, wireless communication link 39 is optional.

In embodiments in which the user calibrates the display screen by moving the sensor to various locations on the screen in response to commands from the data processing system or sensor controller 37, sensor controller 37 can include a web server that can be accessed from any browser. The browser can be run on data processing system 22 or on a separate computer that communicates with sensor 40 via wireless communication link 39. The server can display the locations on display 20 at which the sensor is to be moved. In particular, the sensor can measure the luminescence in the chart display area and compare that to the luminescence in the location in which the sensor resides during normal operation. The measurements can be made for a number of different display luminescence values to provide a calibration curve for translating the measured luminescence to the luminescence in the display area.

A number of considerations dictate the form factor of a sensor according to the present invention. The form of the sensor must allow the sensor to detect the display luminescence without interference from the room lights. In addition, the sensor must not interfere with the patient's view of the chart area. In addition, the sensor must be able to attach to a conventional computer display. In embodiments in which the sensor is to be moved to different locations, the attachment mechanism must be reversible. A clip that positions the sensor on the edge of the monitor can be used in such moveable embodiments. In other embodiments, the sensor assembly can be attached to the monitor by an adhesive.

Figure 4:
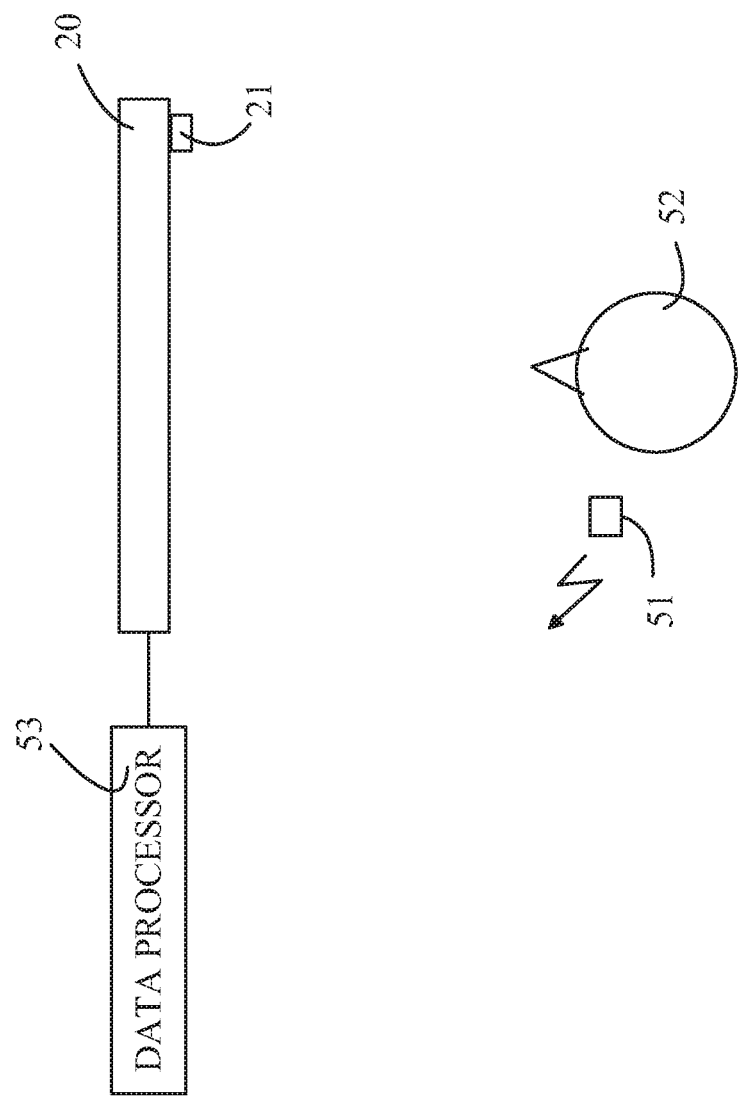
FIG. 4 is a top view of an examining room in which a patient is undergoing an eye examination.

The above described embodiments regulate the luminescence of the display without reference to the ambient light intensity in the room. However, embodiments in which the ambient light intensity at the patient is measured and controlled can also be constructed. Refer now to FIG. 4, which is a top view of an examining room in which a patient is undergoing an eye examination. Patient 52 views display 20 in the manner discussed above. A second luminescence sensor 51 is placed near the patient at approximately the same height as the patient's eyes. In one exemplary embodiment, the second luminescence sensor is placed within 6 inches of the patient's eyes. Luminescence sensor 51 communicates with data processing system 53 to provide a measurement of the luminescence at the patient. Data processing system 53 compares the luminescence measured by luminescence sensor 51 with the allowable range of ambient light levels. If the ambient light is not within the allowed range, data processing system 53 can signal the technician to alter the ambient light in the room by displaying an appropriate message on display 20. In embodiments in which the ambient light in the examining room is under computer control, data processing system 53 can adjust the ambient light to the correct level.

The above-described embodiments address illumination standardization in visual acuity testing. However, the present invention can also be utilized in other tests that present a test pattern of some sort on a monitor to the patient. Tests of peripheral vision, contrast sensitivity and depth perception are examples of such tests. The present invention can also be utilized to maintain a predetermined color temperature of the area of the screen displaying the eye test pattern. In such embodiments, the sensor would include a plurality of sensors having different sensitivities in different wavelength bands. For example, sensors that measure intensity in the red, green and blue color bands can be used to measure color temperature and to servo the display to maintain a predetermined color temperature in addition to a predetermined intensity.

In the above-described embodiments, a single standardized level of illumination is provided; however, the present invention can also be utilized in tests that require multiple illumination levels. In such tests, each of the illumination levels is set by the processor using feedback from the sensor on the monitor.

Figure 5:
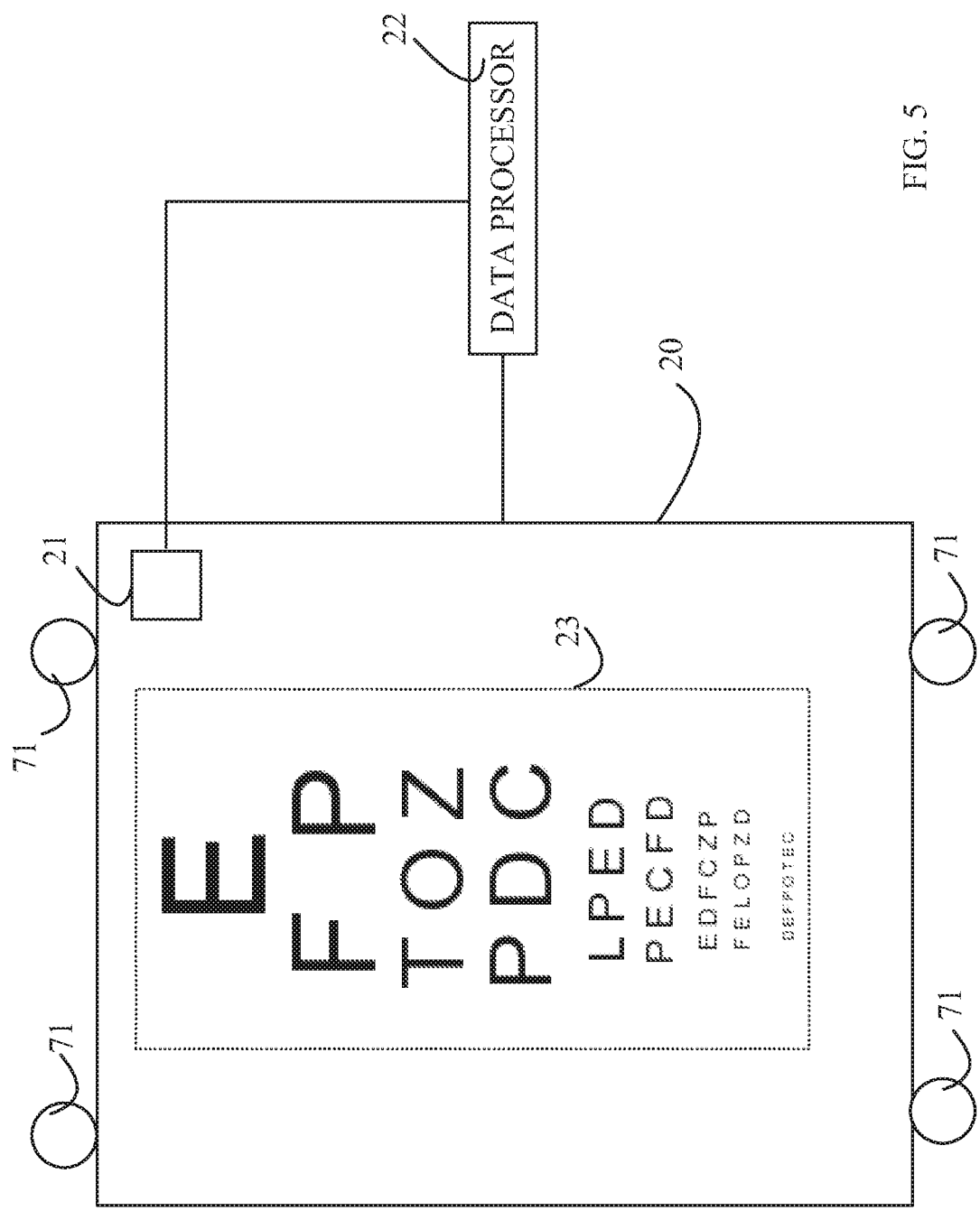
FIG. 5 illustrates a testing system that utilizes a glare source.

The present invention can also be utilized to provide standardization of illumination in testing systems in which a second "glare" source is also utilized. Such arrangements are utilized in tests for cataracts. Refer now to FIG. 5, which illustrates a testing system that utilizes such a glare source. The testing system in FIG. 5 is similar to that shown in FIG. 1; however, in the embodiment shown in FIG. 5, the glare sources 71 are placed on the edge of the monitor. However, embodiments in which the glare sources are on the screen near the test chart can also be constructed. In embodiments of the present invention in which the illumination monitor is moveable, the monitor can be placed on each glare source during a calibration procedure in which the processor adjusts the signal to the glare source to arrive at a predetermined standard glare source level.

The processor that controls the illumination levels in the above-described embodiments could be the same processor that provides the eye chart or other test patterns. Alternatively, a separate processor that only controls the screen illumination or glare source levels could be utilized.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A method of operating a data processing system for displaying an eye test pattern on a computer display to a patient during an eye examination, said method comprising:

causing said data processing system to display said eye test pattern in a chart region of a computer display controlled by said data processing system and characterized by a luminance in regions not displaying said eye test pattern;

measuring an intensity of light leaving said computer display in a sensor region outside said chart region using a display luminance sensor; and adjusting said luminance of said computer display to provide a light level within a predetermined range of light levels based on said measured intensity of light.

2. The method of claim 1 wherein adjusting said luminance comprises receiving said measured intensity by said data processing system and automatically adjusting said computer display in response to said measured intensity.

3. The method of claim 1 wherein said intensity of light is measured by a sensor that views a portion of said computer display and wherein said sensor communicates directly with a user of said data processing system with instructions on changing said luminance of said computer display.

4. The method of claim 1 further comprising providing an ambient light sensor proximal to said patient's eyes that measures an ambient light intensity in a room containing said patient and causing said data processing system to alter said ambient light intensity in said room such that said ambient light intensity in said room is within predetermined limits.

5. The method of claim 4 wherein said ambient light sensor is positioned such that light from said computer display is not directly received by said ambient light sensor.

6. The method of claim 1 further comprising measuring said luminance of said display in said chart region, and measuring said luminance in said sensor region, said data processing system calibrating said measured luminance in said sensor region to said measured luminance in said chart region.

7. The method of claim 6 wherein said display luminance sensor is used to measure said luminance in both said chart region and said sensor region.

8. The method of claim 1 further comprising:
providing a glare light source proximately located to said chart region, said glare light source being characterized by a glare luminescence;
measuring said glare luminescence with said display luminance sensor; and
causing said data processing system to adjust said glare light source such that said measured glare luminescence is within a predetermined range.

9. A vision testing system comprising:
a data processing system that includes a computer display, characterized by a display luminance, on which said data processing system displays an eye test pattern in a chart region of said computer display;
a luminance sensor that measures a light intensity in a sensor region of said computer display, said sensor region being outside of said chart region; and
a display intensity adjustment system that receives an output from said luminance sensor and causes said computer display to change said display luminance such that said output from said luminance sensor output is within predetermined limits.

10. The vision testing of claim 9 wherein said display intensity adjustment system is separate from said data processing system.

11. The vision testing of claim 9 wherein said display intensity adjustment system comprising a program running on said data processing system which automatically adjusts said display luminance in response to said measured light intensity in said sensor region.

12. The vision testing of claim 9 wherein said display intensity adjustment system comprises an interface that instructs a user of said system to manually change said display luminance.

13. The vision testing of claim 9 wherein said luminance sensor reversibly attaches to said computer display.

14. The vision testing of claim 9 wherein said luminance sensor is powered by light received from said computer display.

15. The vision testing of claim 9 further comprising an ambient light sensor positioned proximate to a patient's head that measures ambient light at a location of a patient's eyes and to communicate said measured ambient light to said data processing system.

16. The vision testing of claim 15 wherein said data processing system causes said ambient light to be changed such that said measured ambient light is within predetermined limits.

17. The vision testing of claim 9 further comprising a glare source comprising a light source in close proximity to said chart region, said glare source emitting light characterized by a glare luminescence, wherein said illumination sensor measures said glare luminescence and said data processing system adjusts said glare luminescence such that said glare luminescence is within a predetermined range.

* * * * *